Sept. 18, 1951 J. S. ARMSTRONG Plant Pat. 1,037
EUGENIA PLANT
Filed March 7, 1950
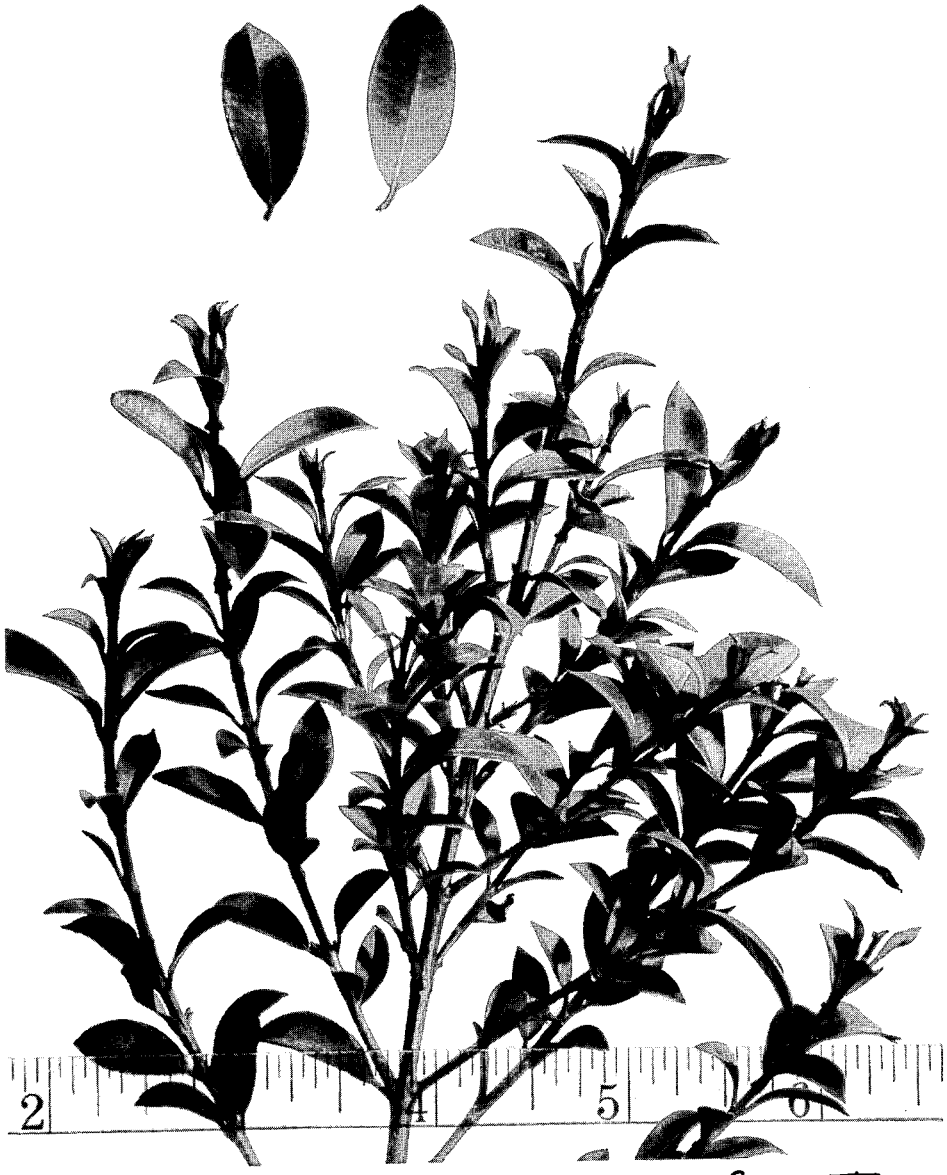
Inventor.
J. S. Armstrong
By: Robb & Robb
Attorneys.

Patented Sept. 18, 1951

Plant Pat. 1,037

UNITED STATES PATENT OFFICE 1,037

EUGENIA PLANT

John S. Armstrong, Ontario, Calif., assignor to Armstrong Nurseries, Inc., Ontario, Calif., a corporation of California Application March 7, 1950, Serial No. 148,230

1 Claim. (Cl. 47—59)

The present invention relates to a new and distinct variety of eugenia plant, originated as a selected seedling of the variety "*Eugenia paniculata* Australis" (unpatented), of which it is a mutant.

This new variety was discovered by me in a cultivated area in my commercial nursery, and in a particular row of plants of the variety "*Eugenia paniculata* Australis" which were being grown from seeds. Consequently, the new variety obviously resulted as a genic change that had taken place at the germinal level in the formation of a seed, which is characteristic of a mutant, as distinguished from a sport in which the genic change takes place at the somatic level, or in other words, in the vegetative tissue. The substantial and important differences between the new variety and its parent were promptly recognized by me and were thereafter confirmed by continued observations and asexual reproduction which have perpetuated and preserved the new variety for all mankind.

To best understand the origination of this new variety, it is desirable to refer somewhat fully to the parent plant type, to more clearly bring out the points of novelty and distinctions applying to the new variety.

The parent plant aforementioned, "*Eugenia paniculata* Australis," is evergreen in habit, with attractive dark-green, leathery leaves having a glossy upper surface texture, and an attractive appearance to the new growth which is yellow-green in color and overlaid with red, the leaves being 22 to 35 mm. long and 15 to 19 mm. wide at the widest portion, with internodes 25 to 45 mm. in length.

While the new variety possesses the desirable characteristics of the parent variety as respects the ever-green habit, coloring and attractive appearance of the leaves and new growth, it is distinguished therefrom primarily by its more dwarf, compact and bushy habit of growth, and by its broad pyramidal shape, which make the new variety more attractive and more useful than its parent, and more suited for planting in limited spaces.

By way of further distinction, the leaves of the new variety are more abundant but somewhat smaller than those of the parent, being from 18 to 24 mm. long and 8 to 12 mm. wide at the widest portion, while the internodes are shorter, being from 10 to 15 mm. in length, when grown under comparable conditions.

Asexual reproduction of the new variety by cuttings at Ontario, California, shows that the foregoing characteristics come true to form and are fixed and transmitted through succeeding propagations.

The accompanying drawings show a specimen plant of the new variety which has attained a typical height of three feet; also detail views of the upper and lower faces, respectively, of a typical leaf specimen, and a portion of the plant which is illustrative of the leafing and branching structure, the latter views being somewhat enlarged and related to an inch-marked scale or rule which indicates their relative size.

The following is a detailed description of the new variety, with color terminology in accordance with Ridgway's Color Standards and Nomenclature, except where otherwise noted with reference to Horticultural Colour Chart. (Observations made at Ontario, California.)

Propagated: It holds its distinguishing characteristics through succeeding propagations by cuttings.

Plant: Small; medium vigor; compact; dwarf; broad pyramidal shape, hardy evergreen.

Leaves: Simple; opposite; firm and glossy; pinnately veined; alternate and parallel. Margins entire, on new growth leaves are oblong-acuminate; becoming at maturity obovate to short-elliptic with an acute apex.

*Length of mature leaf.*—18 to 24 mm., width 8 to 12 mm. wide at widest portion. Petioles short.

*Color.*—Mature leaf—under side—near Light Elm Green, Plate XVII; upper side—between Parsley Green, Plate 00962, page 193 (Horticultural Colour Chart) and Ivy Green, Plate 0001060, page 200 (Horticultural Colour Chart). New growth—under side—near Absinthe Green Plate XXXI, tinted lightly with Acajou Red, Plate XIII; upper side—near Apple Green, Plate XVII, tinted with Acajou Red, Plate XIII, in the marginal regions of the lower two-thirds of the leaves.

Stems: Tip ends of new growth are near Yellowish Oil Green, Plate V, occasionally with a light overlay of Acajou Red, Plate XIII, while the more mature portion of the stems and main trunk become slightly corky and in color near Sayal Brown, Plate XXIX. Internodes are 10 to 15 mm. apart; branching being mostly opposite. Free branching from most nodes on main stems with occasional secondary buds forming branches to make a compact plant.

Flowers and fruit: As yet this variety has not flowered or fruited. Period five years.

I claim:

A new and distinct variety of eugenia plant, characterized by its similarity to its parent "*Eugenia paniculata* Australis," while differing therefrom by its more dwarf, compact and bushy habit of growth and by its broad pyramidal shape, with more abundant but smaller leaves and shorter internodes, substantially as shown and described.

JOHN S. ARMSTRONG.

No references cited.

Certificate of Correction

Plant Patent No. 1037 — September 18, 1951

JOHN S. ARMSTRONG

It is hereby certified that error appears in the above numbered patent requiring correction as follows:

In the drawing, Sheet 1 as shown below should be inserted as part of the Plant Patent—

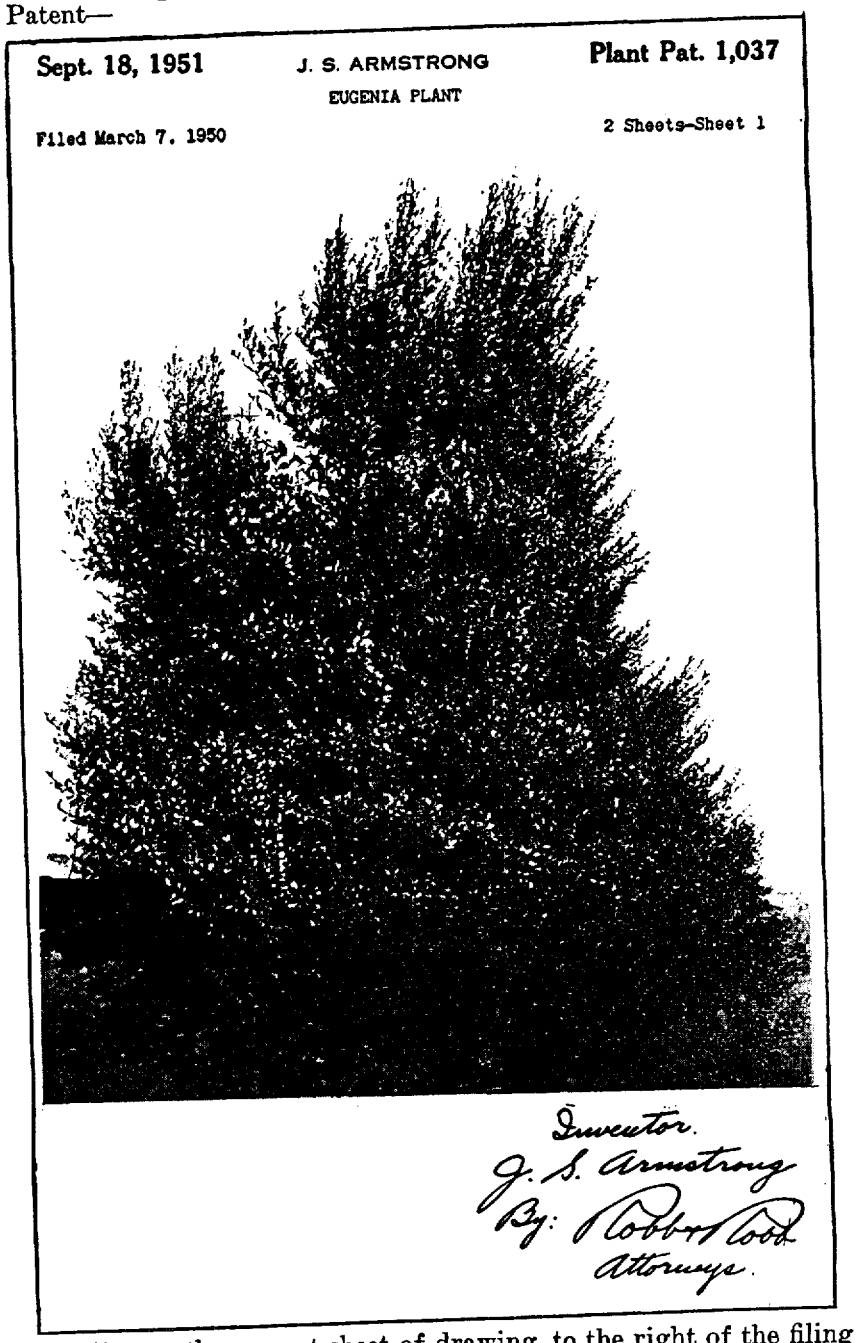

in the heading to the present sheet of drawing, to the right of the filing date insert *2 Sheets—Sheet 2*;

and that the said Letters Patent should be read as corrected above, so that the same may conform to the record of the case in the Patent Office.

Signed and sealed this 17th day of November, A. D. 1953.

[SEAL]

ARTHUR W. CROCKER,
*Assistant Commissioner of Patents.*